United States Patent [19]

Toepel

[11] Patent Number: 5,548,604
[45] Date of Patent: Aug. 20, 1996

[54] COMPACT HAND HELD MEDICAL DEVICE LASER

[76] Inventor: Michael P. Toepel, P.O. Box 343, Pittsfield, N.H. 03263

[21] Appl. No.: 238,712

[22] Filed: May 5, 1994

Related U.S. Application Data

[63] Continuation-in-part of Ser. No. 702, Mar. 19, 1993, abandoned.

[51] Int. Cl.⁶ ........................................................ G02B 6/32
[52] U.S. Cl. .................................. 372/35; 372/72; 372/99
[58] Field of Search ..................................... 372/35, 40, 70, 372/99, 72

[56] References Cited

U.S. PATENT DOCUMENTS

| | | |
|---|---|---|
| 3,821,510 | 6/1974 | Muncheryan . |
| 4,517,974 | 5/1985 | Tanner . |
| 4,564,738 | 1/1986 | Jones et al. . |
| 4,608,980 | 9/1986 | Aihara . |
| 4,644,550 | 2/1987 | Csery et al. . |
| 4,671,273 | 6/1987 | Lindsey . |
| 4,808,789 | 2/1989 | Muncheryan . |
| 4,826,431 | 5/1989 | Fujimura et al. . |
| 4,858,243 | 8/1989 | Bar-Joseph ................. 372/72 |
| 4,894,837 | 1/1990 | DiFonzo et al. ............. 372/72 |
| 4,993,038 | 2/1991 | Nakano et al. .............. 372/72 |
| 5,012,481 | 4/1991 | Casteleiro .................. 372/72 |
| 5,074,861 | 12/1991 | Schneider et al. . |
| 5,121,403 | 6/1992 | Sekino ....................... 372/72 |
| 5,129,897 | 7/1992 | Daikuzono . |
| 5,130,999 | 7/1992 | Maeda et al. ............... 372/72 |
| 5,289,490 | 2/1994 | Taniu et al. ................. 372/72 |

*Primary Examiner*—Rodney B. Bovernick
*Assistant Examiner*—Robert E. Wise
*Attorney, Agent, or Firm*—Stephen G. Matzuk

[57] ABSTRACT

A palm-sized laser device which comprises a laser housing having a cavity situated therein and adaptable optical delivery device in a second housing removably attached to said first housing means. The inventive apparatus is adapted to provide a solid state crystal lase material rod, a lamp within a coupling cavity and a fluid cooling chamber adapted to receive and exhaust coolant from the same end of the laser housing. The inventive combination being generally tubular and overall outside dimensions less than about 2.0 cm in diameter and about 12 to about 20 cm in length. The laser cavity of the present invention includes a coupling element having an eccentric cross-section and is adaptable to include a variety of cross-sections, reflective coatings and/or reflective materials to optimally couple the flashlamp energy to the lase material.

22 Claims, 7 Drawing Sheets

COMPACT HAND HELD MEDICAL DEVICE LASER

RELATED APPLICATIONS

This is a Continuation-in-Part application based on my application Ser. No. 08/000,702, filed Mar. 19, 1993 and now abandoned. This application also includes by reference application Ser. No. 08/149,747 filed Nov. 10, 1993.

FIELD OF THE INVENTION

The present invention relates to laser apparatus, and particularly to small hand-held laser devices typically having medical, industrial and other applications requiring small, mobile laser apparatus.

BACKGROUND OF THE INVENTION

The recent past has seen the use of lasers in a growing number of applications including manufacturing, medical and communications. A number of medical and dental applications have become routine, wherein there exists a need to provide an apparatus which provides ease of use and durability so that in such applications, laser devices can be employed in office settings rather than in surgical environments.

Previously, apparatus have been disclosed which employ smaller dimensioned lase cavities. For example, U.S. Pat. No. 4,664,550 teaches a compact laser apparatus employing a neodymium phosphate glass impulse laser in a compact laser resonator having a liquid cooled laser body. However, the disposition of the laser resonator rod within a glass tube having a reflective coating disposed on the interior walls provides inefficient laser component packaging, complex assembly and inhibited coolant flow. Moreover, this laser apparatus does not optimize the portion of the laser rod that is being resonated.

SUMMARY OF THE INVENTION

The present invention comprises a palm sized laser device having a first housing, a laser cavity therein, and a selectively removable second housing removably attached to the first housing having optical beam shaping and beam delivery elements therein. The inventive apparatus is adapted to provide a solid state crystal lase material resonator rod, and a lamp within a coupling cavity and a coolant fluid flowing therebetween through a folded path having a fluid entrance and a fluid exit at the same end of the first housing. The inventive combination being generally tubular and less than about 2.0 cm in diameter and about 15 cm in length. The preferred embodiment of the present invention provides all electrical and cooling connections through the endcap opposite the beam exit from the cavity, and are removably connected to electrical sources and/or coolant sources by means of quick connect/disconnect device.

The laser cavity optically couples the lamp and the lase material rod by directing the lamp discharge to the lase material rod with an interior reflective surface of a coupling element. Moreover, the reflective surface of the coupling element thus reflects the lamp discharge and can be made of a number of reflective materials, such as polished metals or substrates coated with metallic layers. Furthermore, the reflective surfaces may be dispersive rather than highly specular. Such diffuse surfaces include silver, gold, ceramics and porcelain. A ceramic reflective material is shown in U.S. Pat. No. 4,858,243. Alternately, such surfaces may be coated with diffuse reflective paint such as "KODAK 6080" manufactured by the Eastman Kodak Company of Rochester, N.Y.

Various geometries can be used to couple the lamp with the lase material rod. In cross-section an ellipse with the lase material rod and the lamp in each of the centers of generation will be a preferred embodiment to optimize the lamp discharge. Alternatively, the lamp and lase material rod may be closely coupled using diffuse reflective couplers where specific geometry is less important.

Multiple lamps as well as multiple lase material rods may be employed as well. Alternative geometries that have been effectively tested by the applicant include a simple circle, a slightly compressed circle, which somewhat approximates an ellipse, and an oval 'race track' geometry. Additionally, the applicant has found that a 'teardrop' geometry is especially effective. This geometry allows for the employment of a lase material rod with a smaller diameter than the flashlamp employed. When combined with the use of diffuse reflective materials, the applicant has found that the resulting laser cavity exhibits efficiency as a cavity utilizing a lamp and lase material rod with the same diameters, utilizing specular reflective optical couplers.

The coupling structure employed in the present invention are themselves compact, the housing generally being less than 2.0 centimeters in outside diameter. The reflective surface geometry of the coupling element may have a variety of geometric forms. An elliptical form is one embodiment in that it optimizes the amount of radiation which falls incident on the lase material rod from the flashlamp by holding the lase material rod and the lamp in each of the centers of generation with retainers and epoxy seals or endplates and o-ring seals.

The coupling apparatus comprising reflective surfaces for the lamp energy are formed from multiple interlocking pieces which cooperate to provide the desired geometry to the lase cavity, as well as being formed by using a unitary coupling element. The preferred form employed in the present invention is formed from two Confronting shapes, which cooperate to form the coupling element of the present device.

The present invention provides an efficient, durable laser apparatus capable of being used in a medical office environment. More compact, durable and efficient lasers would provide ease of use and extension of range of utility to medical practitioners especially in dental applications.

BRIEF DESCRIPTION OF THE DRAWING

These and further features of the present invention will be better understood by reading the following Detailed Description of the Invention together with the Drawing, wherein.

DETAILED DESCRIPTION OF THE INVENTION

Figure 1:
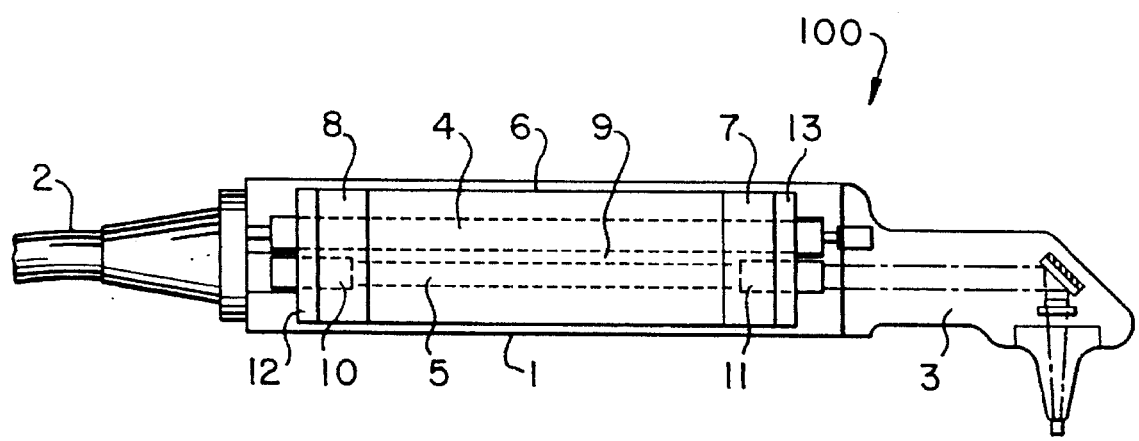
FIG. 1 is a cross-sectional drawing of the laser apparatus with the detachable beam shaping/delivery element attached to the laser cavity apparatus.

The compact laser 100 according to one embodiment of the present invention comprises a first (laser cavity) housing 1 including laser elements with a posterior umbilical 2 carrying electrical power connections and coolant and a detachable output beam shaping/delivery apparatus 3 positioned on the anterior portion of the laser cavity. At least one flash lamp 4, a lase material resonator rod 5; and coupling element 6 (to optimize the electromagnetic discharge from the flashlamp onto the lase material rod) are disposed within the laser housing 1. The flashlamp, lase material resonator rod, and coupling element are held in position relative to one another by means of two pieces, an anterior endcap 7 and a posterior endcap 8 that cooperate with anterior and posterior ends of a cavity housing 1 to hold the lase material rod and the flashlamp in a defined orientation to one another, depending upon the coupling element 6 geometry in order to optimize coupling of lamp discharge to lase material pumping.

Figure 2:
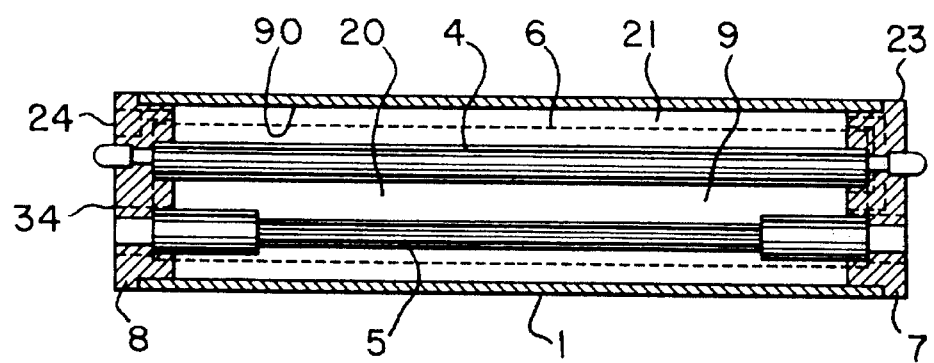
FIG. 2 is a cross-sectional schematic representation of the laser apparatus showing the preferred cooling apparatus.

In addition to optimizing the electromagnetic discharge from the flashlamp onto the resonator rod, the coupling element and cavity housing operate to define a cooling medium flowpath through which a cooling medium is circulated to remove heat generated by the flashlamp. Turning now to FIG. 2, the cooling medium flowpath comprises a first lumen 20 defined by the interior dimensions of the coupling element 6, the cooling medium coming in contact with both the lase material rod 5 and the flashlamp 4 as it flows through the first lumen, and a second lumen 21 that is defined by the exterior dimension of the coupling element 6 and the interior of the cavity housing 1. A coolant stream is introduced into the first lumen 22 from fitting 34 provided in or proximate to the posterior portion of the first lumen. The cooling medium is introduced under sufficient pressure to provide turbulent coolant flow within the first lumen. Cooperating with the anterior portion of the first lumen, is a coolant return path 23 through endcap 7 for allowing exit of the coolant from the first lumen into the second lumen. Proximate to the posterior portion of the second lumen is a cooling medium exit 24 that allows the cooling medium to exit the laser apparatus. A further improvement according to the present invention provides a flat 75 on the outside of section 72 of the coupling element 6 which results in an enlarged channel for tooling fluid flow at 93 within the housing 1 and around the coupling element 6. Further features relating to the fluid flow are provided by the endcaps discussed in FIGS. 3–4B.

Figure 3:
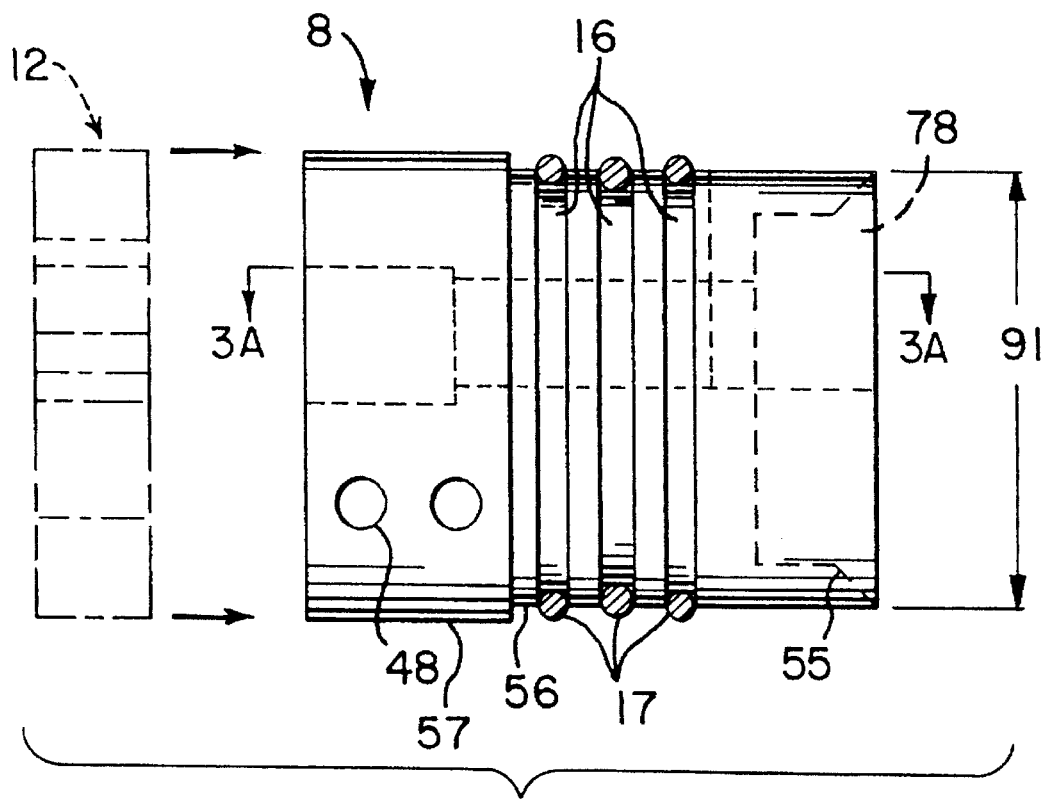
FIG. 3 is an side elevation view of the posterior endcap showing how the coolant is introduced into the lase cavity.
Figure 3A:
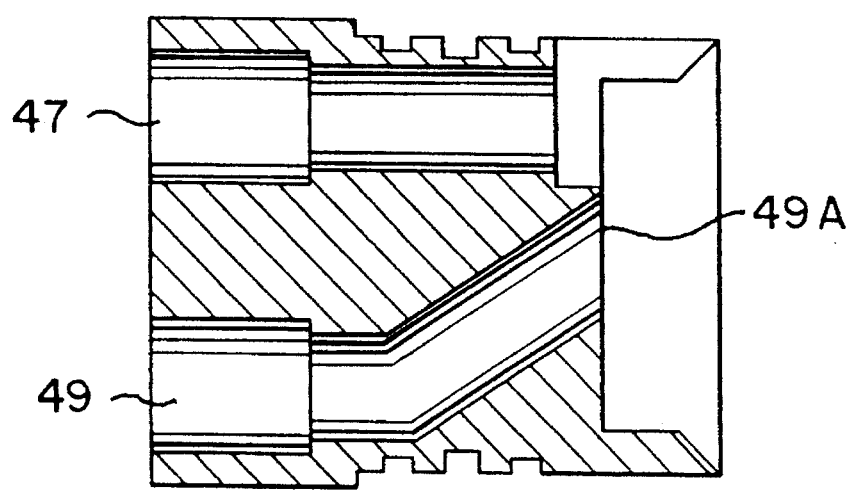
FIG. 3A is a cross-section A of FIG. 3.
Figure 4:
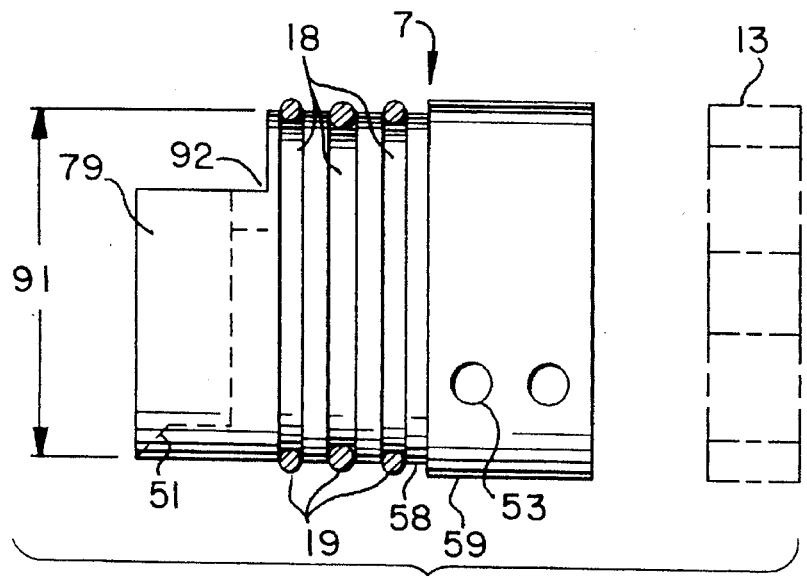
FIG. 4 is the side elevation view of the anterior endcap.
Figure 4A:
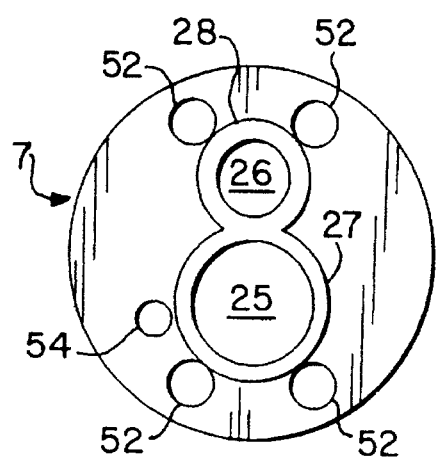
FIG. 4A is the end elevation view of the endcap of FIG. 4.
Figure 4B:
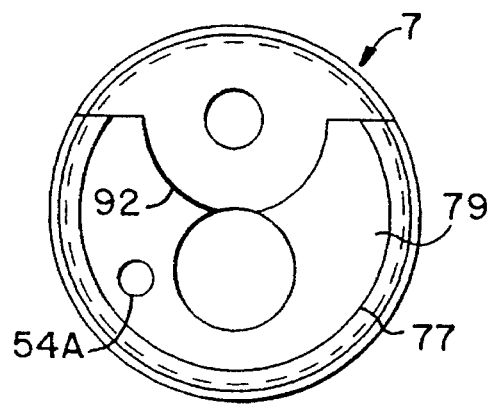
FIG. 4B is the end elevation view of the endcap of FIG. 4 opposite the view of FIG. 4A.

As shown in FIGS. 3–4B, the posterior endcap 8 preferably comprising a conductive material, has openings 42 and 41 for the lase material resonator rod (or extender 10), the flashlamp, respectively. Also provided is an inlet opening 49 for the introduction of coolant into the first lumen in the laser cavity, and an outlet opening 47 for removal of coolant from the laser cavity. The inlet 49 is directed to the region of the cavity 9 between the lamp 4 and lase material 5 by opening 49A, shown in FIG. 3A. At the endcap 7, the fluid return path 23 is provided by recess 92 as shown in FIGS. 4 and 4A.

The dimension 91 of the portion of the endcaps 7 and 8 which are introduced into the end of the housing 1 are less than the interior dimension of the housing 90 (FIG. 2); however, the preferred embodiment provides a slightly larger dimension for the regions 56 and 58 to provide a tight friction fit into the housing 1 which provides the electrical connection between the endcaps via the housing 1, discussed below. The endcaps include a fluid-tight seal to the housing by providing grooves 16, 18 and o-ring seals therein to compress and seal with the housing 1. The seals are compressed by the attachment of endplates 12 and 13. The lamp is excited by connecting directly the 'hot' (non-ground) wire to the end of the lamp 5 near opening 41. The posterior endcap 8 provides elements 48 for securing the electrical (ground return) connections to the other end of the flashlamp 4 by wire connection inserted into openings 46, 46A, which, via the housing and other endcap 8 is connected to the ground return wire at opening 46, 46A. The posterior endcap 8 also has structure for aligning the various components of the laser apparatus by use of alignment pins (not shown) which are placed in alignment bores 43 which penetrate the endcaps 7 and 8 and the coupling element in a fashion to align, in a determined fashion, the flashlamp, the lase material resonator rod and the coupling element.

The anterior endcap 7 also preferably comprising a conductive material, has an opening 25 to allow the generated (output) beam of the resonator rod 5 to pass out of the anterior portion of the laser apparatus. The anterior endcap 7 has a second opening 26 to allow the anterior portion of the flashlamp to be accessible to a second electrical connection 53.

Alternatively, the anterior portion of the flashlamp may be electrically connected to a second (ground return) electrical connection to the posterior endcap opening 54, 54A secured by screws 53 through the electrical conductivity of the materials chosen for the endcaps 7 and 8 and laser cavity housing 1. In this embodiment, the laser cavity housing 1 itself is produced from or treated with one or more materials that cause the laser cavity housing to operate as an electrical conductor eliminating the need to provide a wire through the interior of the unit. Alternately, this second electrical connection would comprise a separate wire (not shown) which would be located outside the laser cavity and not be subjected to the coolant cavity conditions.

The anterior endcap also provides means for aligning the endcap with the other components of the laser apparatus. Alignment bores may be provided in defined positions to the anterior endcap. By way of illustration, alignment bores indicated in FIGS. 4–4B as 52 are be used. Parallel pins (not shown) are inserted through the bores and the bores 43 of endcap 7 to precisely align these components, as well as the optical elements of the laser device.

Figure 5:
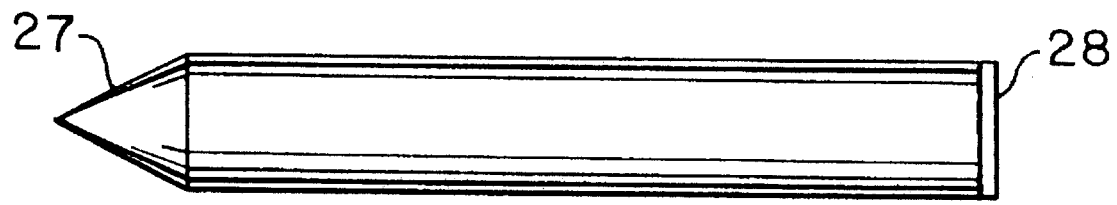
FIG. 5 is a side view of the resonator rod.

The lase material resonator rod itself is manufactured so as to create an optical resonator as required to provide laser operation. In the preferred embodiment, the posterior end of the lase material (resonator) rod 5 is machined as shown in FIG. 5 to create a total reflective "roof" prism. Thus, all laser light directed towards the posterior end 27, of the lase material resonator rod is reflected back into the rod. The anterior end 28 of the rod is treated with a conventional partially reflective mirror coating to reflect a percentage of light back into the rod and allow a percentage of light to exit the resonator rod via the beam shaping/delivery element. Alternately, the lase material rods may have parallel reflective ("plano-plano") reflective ends.

Figure 3B:
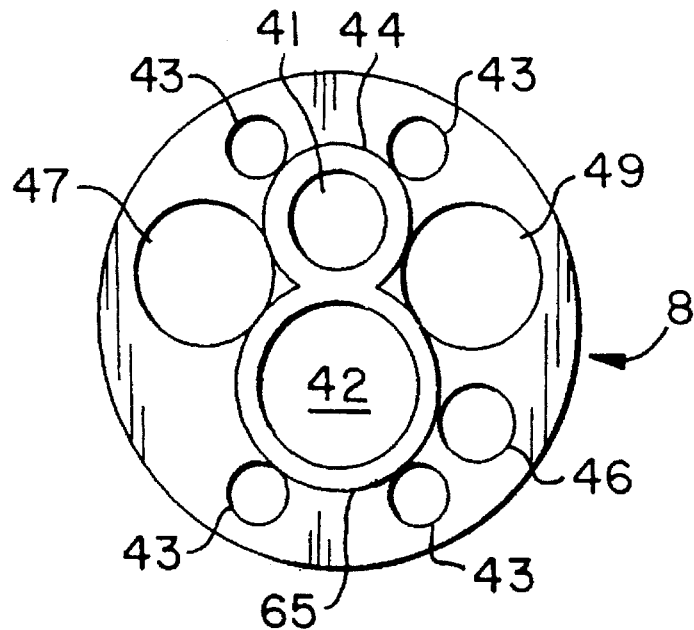
FIG. 3B is an elevation view of the endcap of FIG. 3.
Figure 3C:
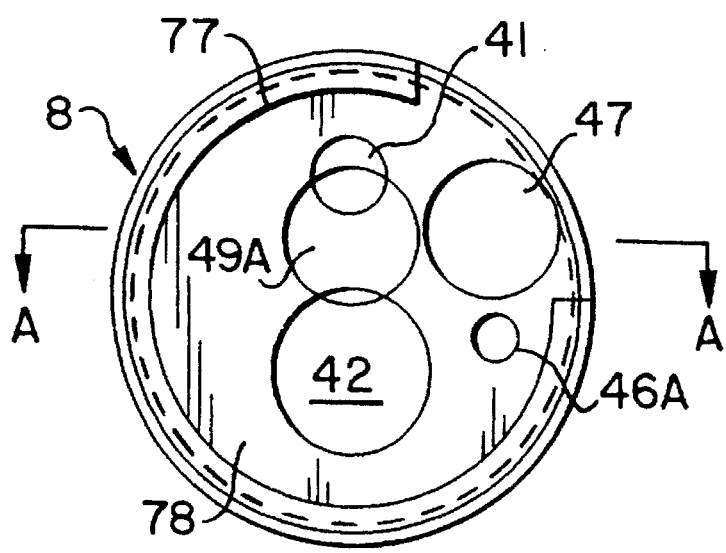
FIG. 3C is an elevation view of endcap of FIG. 3 opposite the view of FIG. 3B.
Figure 6:
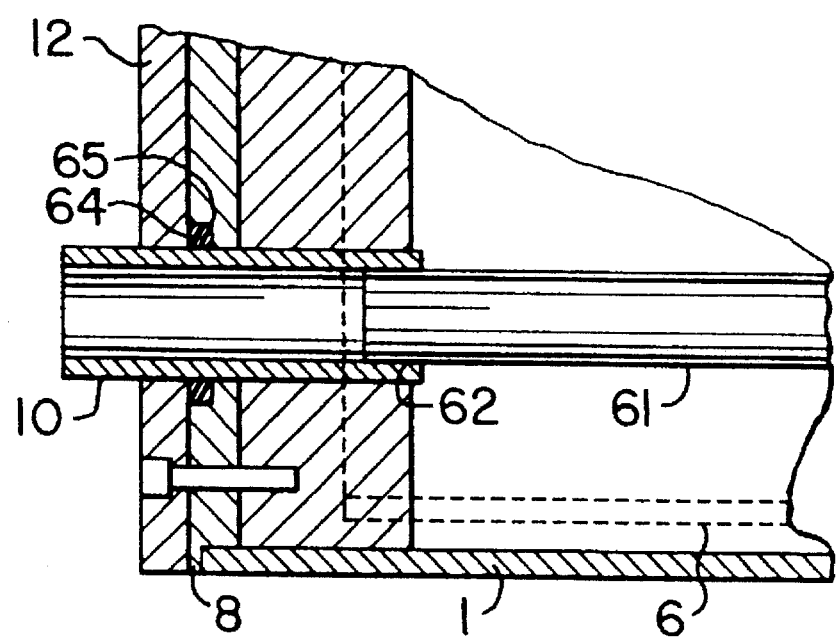
FIG. 6 is a cross-sectional view of an endcap showing the resonator rod, an extender and associated geometry.

Turning now to FIG. 6, the apparatus may further comprise optically transparent resonator rod extenders, 10 and 11. These extenders allow a greater portion of the resonator rod 61 to be irradiated or pumped by flashlamp 4. Both the anterior and posterior endcaps 7 and 8 respectively further comprise sealing element 64 to prevent the cooling medium from escaping from its prescribed flowpath and out of the resonator rod and flashlamp opening. The sealing element may take the form of an o-ring seal 64 secured by retainer plate 12 or may take the form of an adhesive that fixes the lamp and resonator rod in position. If an o-ring seal is used, an o-ring groove 65 (27 in endcap 7) provides a path for the o-ring approximately equal to the circumference of the resonator rod extender. The o-ring seal fits between the rod extender 10, the interior surface of the endcap 8 and retainer plate 12. Retainer plate 12 compresses the o-ring and creating a fluid-tight seal. Similarly a second sealing element is utilized to seal the endcap 8 housing 1 joint to prevent the escape of cooling medium. This sealing element may also take the form of an o-ring, an adhesive joint or even a hermetic weld. Also as shown in FIGS. 3B and 4A, o-ring grooves 44 and 28 receive an o-ring (not shown) to provide a fluid-tight lamp 4 seal. The seals are compressed by endplates 12 and 13, shown in phantom in FIGS. 3 and 4. Alternately, epoxy may be applied to form the seal(s).

The laser rod 61 is sealed by means of optically transparent adhesive 62 between the rod and the internal surface of the rod extender 10 and similarly with extender 11. Alternatively, the holding structure may be a chemical bonding agent applied to the exterior surface of resonator rod extenders 10 and 11 and used to secure the rod extenders to endcaps 7 and 8. The holding structure for orienting the flashlamp 4 may also be a chemical bonding agent applied to the exterior surface of the flashlamp and securing it to endcaps 7 and 8. The chemical bonding agent is preferably optically transparent in order to maximize the irradiation of the resonator rod.

Figure 7:
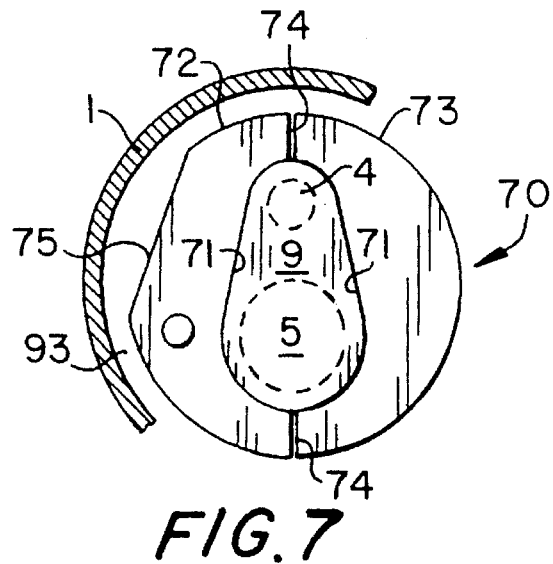
FIG. 7 is a end view of a two piece coupling element.
Figure 7A:
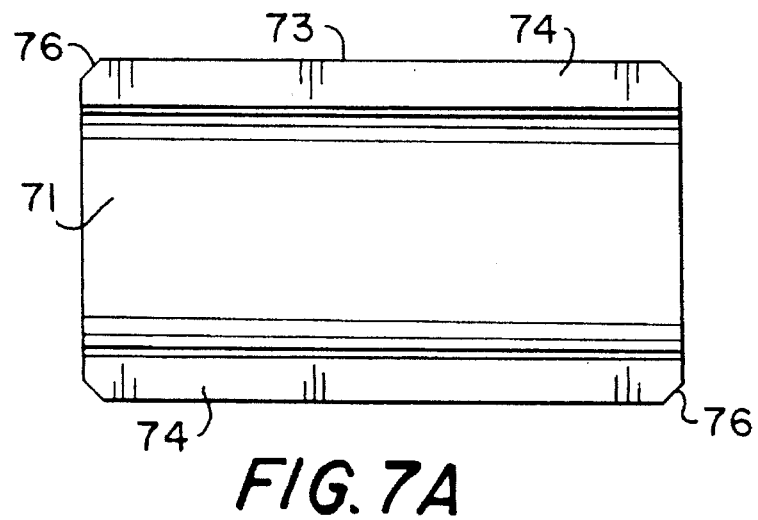
FIG. 7A is a side view of one coupling element.

The light coupling element 6 comprises one or more pieces, and may have a number of cross-sectional geometries. A two-piece (72, 73) coupling element is shown in FIG. 7. The light coupling element is seated within recesses 78 and 79 of endpieces 8 and 7 respectively, which act to hold and center the element 6 within the housing 1. Chamfered edges 51, 55 and 76 serve to guide the pieces together. An elliptical cross-section, with points of generation coincident with the centers of the lase material resonator rod 5 and the flashlamp 4, is a simple example of such a cross-section to optimize the lamp discharge. Various geometries can be used to couple the lamp with the lase material rod. Multiple lamps as well as multiple lase material rods may be employed as well. Alternative effective geometries include a simple circle, a slightly compressed circle, which somewhat approximates an ellipse, and a race track geometry. The coupling element employed in the present invention is compact, generally allowing the external diameter of housing 1 to be less than approximately ¾ inch in outside diameter. Moreover, further aspect of the present invention provides a 'teardrop', or asymmetric coupling element interior cross-section geometry is especially effective (as shown in FIG. 7), wherein the distance between the coupling element 6 reflective surface 71 and the outer surface of lamp 4 being the same (e.g. 1.5 mm) as the distance between the coupling element 6 reflective surface 71 and the outer surface of the lase material 5. Since the lamp 4 and the lase material 5 typically have different diameters, a 'teardrop' cavity 9 cross-section is formed.

The coupling element 6 in the preferred embodiment comprises multiple confronting and/or interlocking pieces 72 and 73 that cooperate to provide the desired geometry to the laser cavity 9 in a unitary structure. The preferred form employed in the present invention is formed from two complementary confronting shapes 72, 73, which cooperate with the coupling element holders to form the lase cavity of the present device, which is disposed within the first housing 1. In addition to provide improved ergonomic aspects to the device, the housing 1 may also function to shield the user from electrical connections and from heat generated by the operation of the laser.

The coupling element 6 has an interior reflective surface 71 that operates to reflect the lamp 4 discharge and can be made of a number of reflective materials. The reflective surfaces may be dispersive or highly specular. Alternatively, the lamp and lase material resonator rod may be closely coupled using diffuse reflective couplers where specific geometry is less important.

Figure 8:
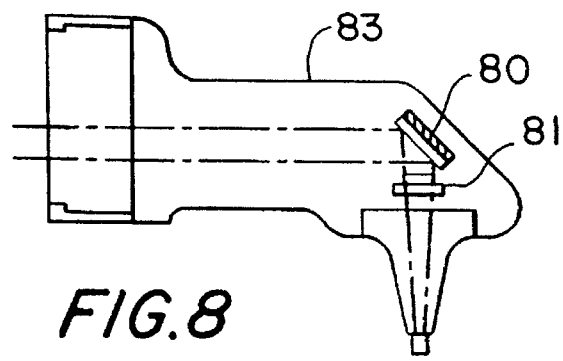
FIG. 8 is a schematic of the detachable beam management attachment.

The device further comprises an adaptable and removable beam shaping/delivery element 3 as shown in FIG. 8. This beam shaping/delivery element 3 allows the user to interchange beam characteristics such as focal length or effective beam width at a given distance by replacing one beam shaping/delivery element with another. These beam shaping/delivery elements are removably attached to the laser cavity in a manner similar to the mating of the grooved end pieces into the housing with o-rings. Moreover, the beam shaping/delivery elements may be provided in a set of several different beam shaping/delivery elements to be readily interchanged. In one embodiment, the beam shaping/delivery element includes a second housing 83 adapted to hold the defined optical elements 80, 81. For instance a mirror 80 may be used to bend the laser beam from its path incident to the resonator rod. A lens 81 incident with the reflected beam focuses the beam at a designated focal length. Other combinations of optical elements may be employed as well, and include a set of elements designed to broaden the beam to a designated width at a defined beam length from the device. A flexible means for altering the path of the beam produced by the apparatus, such as one that might employ optical fibers, is also within the scope of the invention.

It should be noted that a principal advantage of the present invention is that it allows for an extremely compact assembly. A laser apparatus about 2.0 cm in diameter and about 15 cm in length, including the detachable beam shaping/delivery apparatus, can be made according to the present invention that is durable, easy to manufacture, and flexible in regards to performance modification.

Figure 9:
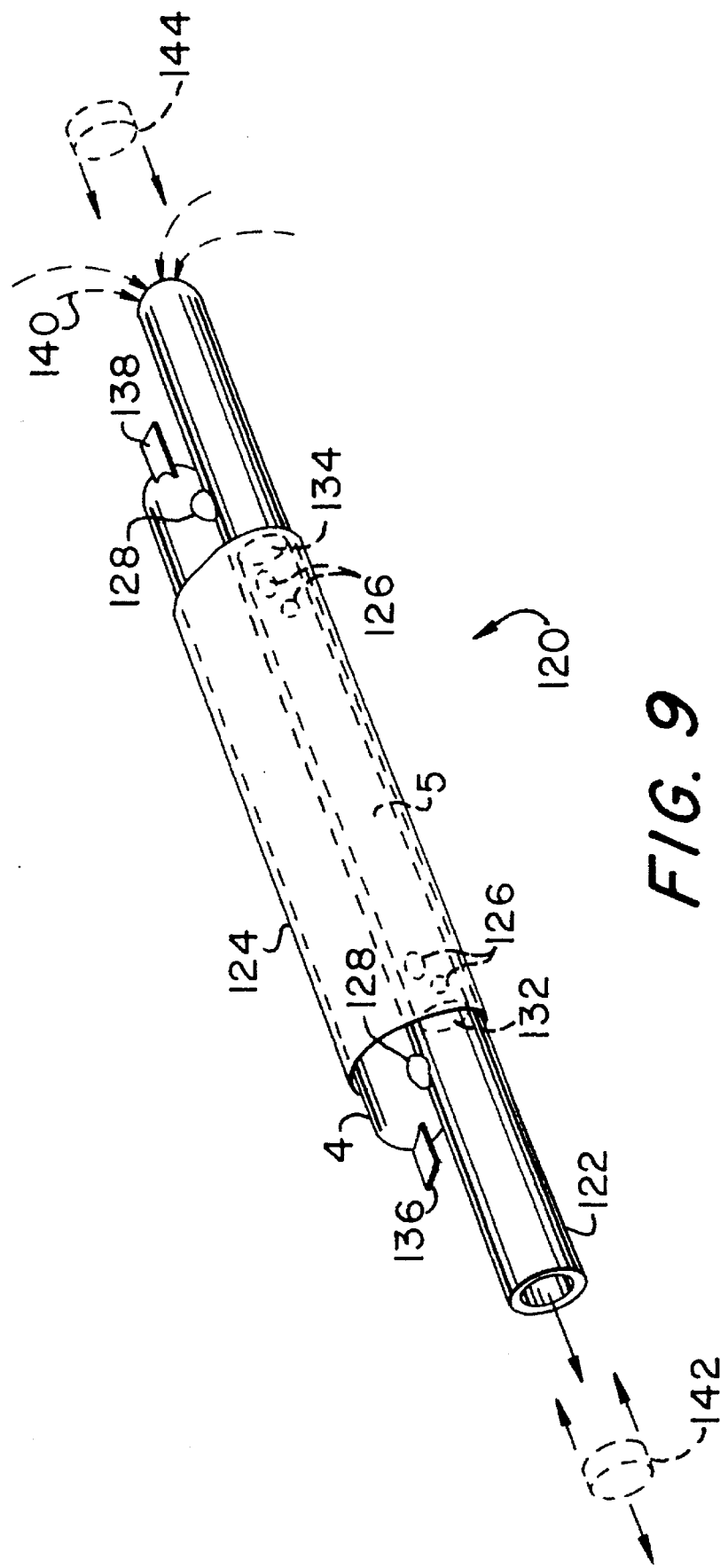
FIG. 9 is a perspective drawing of an alternate embodiment of the present invention having a laser rod mounted in a glass tube.

A further embodiment of the present invention is shown in FIG. 9, comprising a flashlamp 4, laser resonator rod 5 retained within a tube 122 and a coupling element 124 surrounding the flashlamp 4 and the tube in close proximity. The tube 122 typically comprises a pyrex glass or clear fused quartz tube which is optically transparent at the wavelength used to pump the laser resonator rod 5 by the flashlamp 4. The tube 122 is typically bonded to the flashlamp with a soft epoxy bonds 128, and retains the laser resonator rod 5 with soft or hard epoxy bonds 126 applied to the laser resonator rod through opposing apertures (not shown) in the tube 122.

The laser resonator rod 5 may be less than the inside diameter of the tube 122 to permit a flow 140 of cooling fluid, such as filtered air, therethrough.

The laser resonator rod typically has a reflective ends 132, 134 providing the path through the laser resonator rod necessary to achieve lasing. Alternately, reflector elements 142 and 144 are secured to the ends of the tube 122 by epoxy or other connection and are disposed in the desired orientation to achieve lasing in the laser resonator rod when suitably pumped. The coupling element is typically a conformable reflector, such as a silvered film which is tightly wrapped around the flashlamp 4 and the tube 122. The assembly comprising the flashlamp 4, laser resonator rod 5, tube and coupling element 124 is typically retained in a housing such as the housing 1 of FIG. 1. The assembly is retained by one or more structures similar to the endcaps 7 and 8, which are affixed to the housing and to either or both the electrical connections 136, 138 of the flashlamp 4 and the tube 122.

Modifications and substitutions by one of ordinary skill in the present invention is within the scope of the present invention which is not to be limited except by the claims which follow.

What is claimed:

1. A compact laser apparatus comprising:
    a laser cavity housing having an interior and an exterior surface;
    a laser resonator rod having anterior and posterior ends;
    a flashlamp having anterior and posterior electrical connections;
    a coupling means having an interior reflective surface disposed towards said resonator rod and said flashlamp and an exterior surface disposed towards said laser cavity housing;
    first and second means for orienting and holding said resonator rod, said flashlamp and said coupling means to provide optical pumping of said resonator rod by said flashlamp;
    a means for circulating a cooling medium through said laser apparatus in a first direction along said laser resonator rod and said flashlamp and in a second direction along the exterior surface of said coupling means and the interior surface of the laser cavity housing, for removing heat generated by said flashlamp during laser operation; and
    a beam shaping/delivery apparatus removably connected to the laser cavity housing to receive the laser emissions of said laser resonator rod.

2. The apparatus of claim 1 wherein said removable beam shaping/delivery apparatus connected to said laser cavity housing to receive the laser emissions of said laser resonator rod includes at least one of a lens and a mirror to provide a formed beam therefrom.

3. The apparatus of claim 2 wherein said removable beam shaping/delivery means is removably attached to said exterior vessel by a precision friction lock mechanism.

4. The apparatus of claim 1 wherein said resonator rod comprises a solid state lase material rod, said posterior end of said rod having a total reflective roof prism and said anterior of said rod being treated with a partially reflective mirror coating.

5. The apparatus of claim 1 wherein said interior reflective surface of said coupling means is a diffuse reflective surface.

6. The apparatus of claim 1 wherein said interior reflective surface of said coupling means being highly specular.

7. The apparatus of claim 1 wherein said first and second means for orienting and holding said resonator rod, said flashlamp, and said coupling means comprises posterior and anterior endcaps, each comprising a means for precisely holding said resonator rod, a means for precisely holding said flashlamp, means for accurately holding said coupling means, and a sealing means to retain the cooling means within the laser apparatus.

8. The apparatus of claim 7 wherein said means for precisely holding said resonator rod is a resonator rod bore through each of said endcaps, said bore having a diameter approximately equal to the outer diameter of said resonator rod.

9. The apparatus of claim 7 wherein said means for precisely holding said flashlamp is a flashlamp bore through each of said endcaps, said bore having a diameter approximately equal to the outer diameter of said flashlamp.

10. The apparatus of claim 7 wherein said sealing means is a plurality of o-ring seals circumscribing said resonator rod bore and said flashlamp bore and at least one retainer plate to compress said o-ring seals.

11. The apparatus of claim 7 wherein said sealing means being a chemical bonding agent.

12. The apparatus of claim 1 wherein said anterior flashlamp electrical connection is connected to said laser cavity and wherein said laser cavity is electrically conductive and connected to said power source umbilical.

13. The apparatus of claim 1 wherein said cooling medium circulating means comprises a cooling passage having an inlet through the first of said orienting and holding means into a first lumen formed by said interior surface of said coupling means, a return means through the second of said orienting and holding means into a second lumen formed by the exterior surface of said coupling means and the interior surface of said laser cavity housing, and an outlet means through the first of said orienting and holding means.

14. The apparatus of claim 1, wherein the interior reflective surface of said coupling means defines an interior region a longitudinal dimension parallel to said flashlamp and said lase material disposed therein and has an eccentric cross-section through a plane perpendicular to said longitudinal dimension, wherein said eccentric cross section provides a greater distance between said lase material and said interior reflective surface than between said flashlamp and said interior reflective surface.

15. A compact laser apparatus comprising:
    a laser cavity housing having an interior and an exterior surface;
    a laser resonator rod having anterior and posterior ends;
    a flashlamp;
    a coupling means having an interior reflective surface disposed towards said resonator rod and said flashlamp and an exterior surface disposed towards said laser cavity housing;
    first and second means for orienting and holding said resonator rod, said flashlamp and said coupling means to optimize the degree to which said flashlamp pumps said resonator rod, wherein
    said resonator rod comprises a solid lase material and at least one rod extender.

16. The apparatus of claim 15 wherein said rod extender is optically transparent, has an inner diameter approximately equal to the outer diameter of said resonator rod, and is connected at a first end to said orienting means and at a second end to said resonator rod, using a transparent chemical bonding agent.

17. A compact laser apparatus comprising:

a laser resonator rod having anterior and posterior ends;

a flashlamp having anterior and posterior electrical connections;

a tube retaining said laser resonator rod therein, wherein said tube is disposed substantially parallel to said flashlamp and wherein said tube is optically transparent at the wavelength said flashlamp pumps said laser resonator rod;

a coupling means having an interior reflective surface disposed toward said resonator rod and said flashlamp, wherein said coupling means comprises a unitary reflector wrapped around over said flashlamp and said tube.

18. The apparatus of claim 17, wherein said unitary reflector comprises a silvered foil.

19. The apparatus of claim 17, wherein said laser resonator rod has an outside diameter and said tube has an inner diameter greater than said laser resonator rod outer diameter sufficient to permit a cooling fluid to pass thereover.

20. The apparatus of claim 17, further including reflective elements disposed on polished surfaces of the ends of said laser resonator rod.

21. The apparatus of claim 17, further including reflective elements disposed on the ends of said tube providing a optically reflective path through said laser resonator rod.

22. The apparatus of claim 21 further including a housing surrounding said flashlamp, said laser resonator rod and said unitary reflector, wherein said housing is retained to one of said flashlamp and said tube.

* * * * *